United States Patent [19]

Nakanishi

[11] Patent Number: 5,217,327
[45] Date of Patent: Jun. 8, 1993

[54] GROUND REFORMING METHOD WITH A HARDENING MATERIAL MIXED AND INJECTED AT A SUPER HIGH PRESSURE AND REFORMING DEVICE OF SAME

[75] Inventor: Wataru Nakanishi, Machida, Japan

[73] Assignee: N.I.T. Co., Ltd., Japan

[21] Appl. No.: 870,232

[22] Filed: Apr. 20, 1992

Related U.S. Application Data

[63] Continuation of Ser. No. 477,125, Feb. 7, 1990, abandoned, Continuation-in-part of Ser. No. 375,616, Jul. 5, 1989, abandoned.

[30] Foreign Application Priority Data

Nov. 18, 1988 [JP] Japan .................. 63-292078

[51] Int. Cl.⁵ .................. E02D 3/12
[52] U.S. Cl. .................. 405/269; 405/266
[58] Field of Search .......... 405/266, 267, 268, 269

[56] References Cited

U.S. PATENT DOCUMENTS

| | | | |
|---|---|---|---|
| 3,608,318 | 9/1971 | Levy et al. | 405/269 X |
| 4,624,606 | 11/1986 | Nakanishi et al. | 405/269 |
| 4,640,649 | 2/1987 | Nakanishi | 405/237 |
| 4,786,212 | 11/1988 | Bauer et al. | 405/269 |
| 5,123,782 | 6/1992 | Yoshida et al. | 405/269 X |
| 5,141,366 | 8/1992 | Ishida et al. | 405/266 X |

FOREIGN PATENT DOCUMENTS

| | | | |
|---|---|---|---|
| 305235 | 4/1918 | Fed. Rep. of Germany | 405/269 |
| 3737259 | 3/1989 | Fed. Rep. of Germany | 405/269 |
| 142816 | 11/1980 | Japan | 405/269 |
| 24052 | 6/1981 | Japan | 405/269 |
| 51323 | 3/1982 | Japan | 405/269 |

Primary Examiner—Dennis L. Taylor
Assistant Examiner—John A. Ricci
Attorney, Agent, or Firm—Joseph W. Berenato, III

[57] ABSTRACT

A ground reforming method comprises a first step for inserting an injection rod into ground to be reformed, which injection rod includes a first conduit and a second conduit surrounding the first conduit, and a first injection nozzle communicated with the first conduit and a second injection nozzle surrounding the first nozzle and communicated with the second conduit; a second step for feeding first component of an instantaneous hardening type hardening material into the first conduit of the injection rod and a second component of the hardening material (or compressed gas) into the second conduit; and a third step for injecting the first component and the second component (or compressed gas) at a super high pressure through the first and second nozzles to mix each other with moving back the injection rod from the inserted portion with revolving.

11 Claims, 1 Drawing Sheet

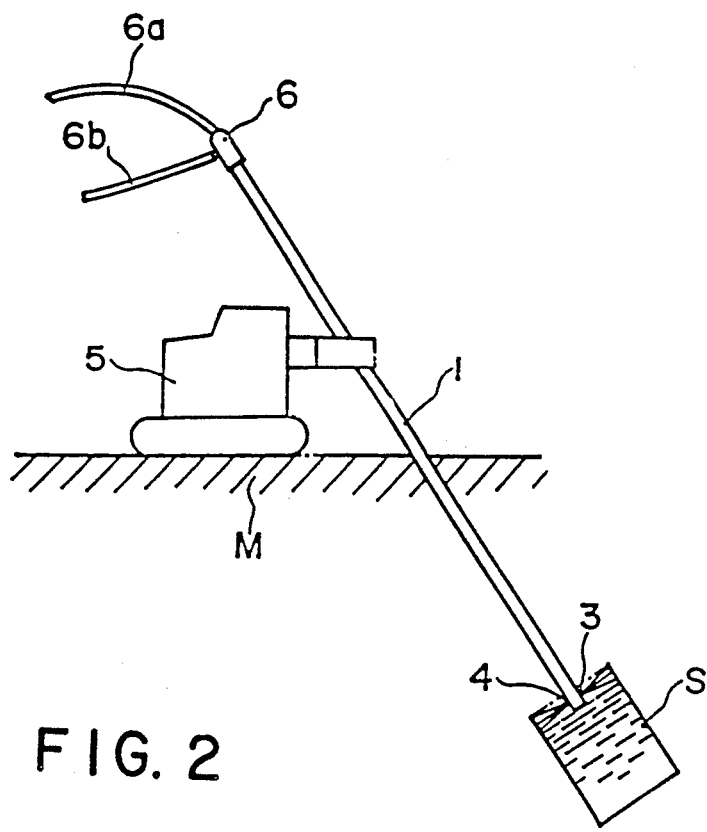
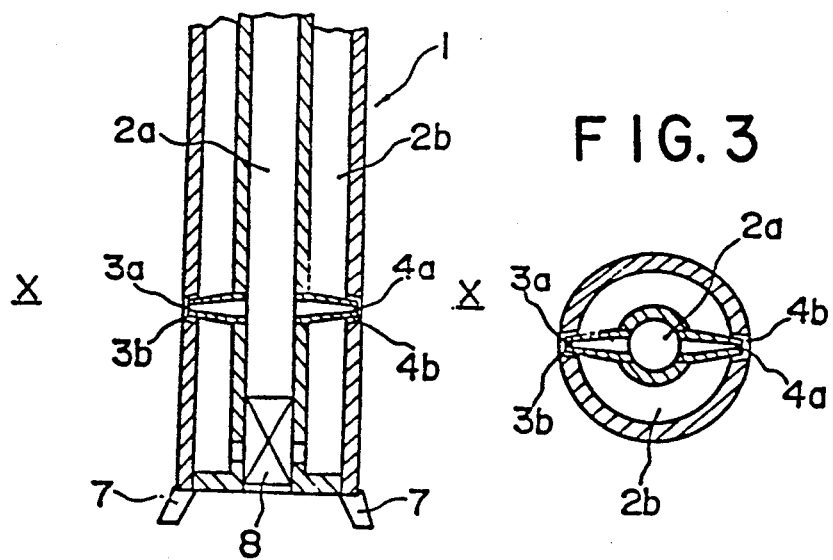

GROUND REFORMING METHOD WITH A HARDENING MATERIAL MIXED AND INJECTED AT A SUPER HIGH PRESSURE AND REFORMING DEVICE OF SAME

This is a continuation of co-pending application Ser. No. 07/477,125, filed on Feb. 7, 1990 now abandoned which is a continuation-in-part of application Ser. No. 07/375,616, filed Jul. 5, 1989, now abandoned.

BACKGROUND OF THE INVENTION

1. Field of the Invention

The present invention generally relates to a method for reforming ground-condition by using an instantaneous hardening type hardening material or a combination of a slow hardening type hardening material and a high pressure air to reform soft ground conditions and harden foundations of building sites. More particularly, two components of the instantaneous hardening type hardening material are injected into the ground through a two fluid mixing nozzle at the same occasion.

Further, the present invention relates to a device for reforming ground-condition by using the two fluid mixing nozzle.

2. Description of the Prior Art

Conventionally, various ground reforming methods using a hardening material jet have been provided. In these methods, high pressure and high speed jet injection has been applied to only a slow hardening type hardening material, on the other hand an instantaneous hardening type hardening material has been injected under a low pressure approaching ambient pressure. The high pressure injection has been conducted at highest 200 kg f/cm$^2$, and no injection device adapted for higher injection pressures has yet been proposed.

The instantaneous hardening type hardening material can not be used for such high pressure injection type ground reforming method because the instantaneous hardening type hardening material is composed of two separated liquids which should be mixed after injection. If these two liquids are mixed prior to injection, the hardening material will be wholly or partially hardened in an injection pump or pipe. Therefore the high pressure injection method has employed the slow hardening type hardening material which requires a long period to achieve hardening. However, the slow hardening type hardening material will sometimes cause problems owing to its slow hardening speed. For example, if the injection amount is increased, the slow hardening type hardening material will flow backwards to leak out of the injection pipe or the like. Special injection angles such as horizontal injection or upward injection, will remarkably cause such problems and thus can not employ the high pressure injection method.

In the high pressure injection method, reaction force will be generated at the injection nozzle as the injection pressure is increased, and the reaction force will be applied to an injection rod. Revolving motion of the injection rod will be affected by the reaction force and as a result the injection rod will result in serious trouble.

BRIEF SUMMARY OF THE INVENTION

It is therefore an object of the present invention to provide a ground reforming method which can overcome the above described problems.

It is another object of the present invention to provide a ground reforming method available for any type hardening material.

It is a further object of the present invention to provide a ground reforming method which employs an instantaneous hardening type hardening material injected at a super high pressure of at least 200 kg f/cm$^2$ to reform soft ground and harden foundations of building sites.

It is a further object of the present invention to provide a ground reforming device adapted for the above method.

To accomplish the above objects, the ground reforming method according to the present invention comprises a first step of inserting an injection rod into ground to be reformed, which injection rod includes a first conduit and a second conduit surrounding the first conduit, and a first injection nozzle communicating with the first conduit and a second injection nozzle surrounding the first nozzle and communicating with the second conduit; a second step of individually feeding first and second components of an instantaneous hardening type hardening material or a slow hardening type hardening material and a high pressure air into the first and second conduits of the injection rod; and a third step of injecting the first and second components or the slow hardening type hardening material and the high pressure air under a super high pressure through the first and second nozzles to mix each other with moving back the injection rod from the inserted portion with revolving.

According to another aspect of the present invention, the ground reforming device comprises an injection rod including a first conduit through which a first component of an instantaneous hardening type hardening material or a slow hardening type hardening material is fed and a second conduit through which a second component of the instantaneous hardening type hardening material or a high pressure air is fed, the second conduit surrounding the first conduit; a first injection means communicates with the first conduit, which means includes a pair of first injection nozzles oppositely arranged in a side wall of the injection rod near its top; a second injection means communicates with the second conduit, which second injection means includes a pair of second injection nozzles surroundingly arranged around the first injection nozzles; and a drive means for supporting and driving the injection rod to revolve and move reciprocally.

The first and second components of the instantaneous hardening type hardening material are respectively fed into the first and second conduits without mixing each other under a super high pressure. These components are injected through the injection nozzles and suddenly mix with each other to form a hardening material jet.

In the case of the combination of the slow hardening type hardening material and he high pressure air, the slow hardening type hardening material nd the high pressure air are also isolatedly fed into the first and second conduits, and injected through he injection nozzles to mix hc hardening material jet and the air jet. The hardening material jet is wrapped with the air bubbles and forcibly transported to a wide range by dynamic rupture effect generated when the bubbles are ruptured. The jet injected from the opposite nozzles can absorb reaction force generated by injection from the other side. As the injection rod is revolving and moving back from the inserted position, the ground surrounding the injection rod is reformed into a cylindrical hardened layer.

Other and further objects of this invention will become obvious upon an understanding of the illustrative embodiment about to be described or will be indicated in the appended claims, and various advantages not referred to herein will occur to one skilled in the art upon employment of the invention in practice.

BRIEF DESCRIPTION OF THE DRAWING

FIG. 1 is a schematic illustration showing one example of working state where the injection rod is inserted in ground;

FIG. 2 is a vertical cross sectional view showing the top portion of the injection rod according to the present invention; and FIG. 3 is a cross sectional view taken along the line X—X in FIG. 2.

DETAILED DESCRIPTION OF THE PREFERRED EMBODIMENT

A preferred embodiment of the present invention will be explained in conjunction with the accompanying drawings.

In FIG. 1, the reference numeral 1 denotes an injection rod which includes a first conduit 2a and a second conduit 2b isolated each other as shown in FIG. 2. The first conduit 2a is arranged in a core of the injection rod 1 and is surrounded by the second conduit 2b. The first conduit 2a communicates with center nozzles 3a and 4a which are oppositely arranged in the side wall near the tip of the injection rod 1 and extend radially with respect to the longitudinal axis of the injection rod 1. As shown in FIG. 3, the second conduit 2b communicates with surrounding nozzles 3b and 4b whose annular openings surround respectively the center nozzles 3a and 4a.

The injection rod 1 is supported by a drive unit 5 which revolves and reciprocally moves the injection rod 1. The injection rod 1 is further connected to a first feeding pipe 6a and a second feeding pipe 6b through a swivel joint 6. Component A of an instantaneous hardening type hardening material is fed into the first conduit 2a from the first feeding pipe 6a, and component B of the instantaneous hardening type hardening material is fed into the second conduit 2b from the second feeding pipe 6b. Alternatively, a slow hardening type hardening material per se is fed into the first conduit 2a from the first feeding pipe 6a, and compressed gas such as air is fed into the second conduit 2b from the second feeding pipe 6b.

The first and second feeding pipes 6a and 6b are connected to a compressor, not shown in the drawings, to generate a super high pressure fluid such as the instantaneous hardening type hardening material or gas. The compressor includes a piston, a valve chamber, cylinder and a pressure sensitive member for transmitting pressure from the cylinder to the valve chamber. The pressure sensitive member is composed of active oil having different specific gravity than the instantaneous hardening type hardening material, and an elastic film actuated by the active oil. The active oil is moved in response to the reciprocal motion of the piston so that the hardening material can be introduced into the valve chamber and then discharged out of the chamber by the high pressure In this compressor the hardening material is isolated from the piston through the pressure sensitive member Therefore the hardening material can be discharged without energy loss caused by the friction between the piston and the hardening material The valve chamber is provided with an inlet through which the hardening material is introduced into the chamber and an outlet through which the hardening material is discharged to the feeding pipe. Each of the inlet and the outlet are provided with a valve box whose valve seat is sectionally formed in a half spherical recessed shape. The valve seat is further formed with a plurality of orifices in its axial direction. The valve seat receives a valve member formed in a spherical shape adapting for the valve seat. The valve member is always urged toward the valve seat by a spring. This valve mechanism employing the spherical valve member can promote to increase the discharging pressure.

The drive unit 5 is preferable to be designed so that the drive angle for the injection rod 1 can be freely changed and the drive unit 5 per se can be moved without an additional drive mechanism.

The top of the injection rod 1 is provided with an excavating member 7 and a lubricating unit 8 as shown in FIG. 2. The lubricating unit 8 will discharge lubricant to assist the excavating work of the excavating member 7.

Operation of the ground reforming method according to the present invention will be described. The injection rod 1 while revolving and discharging the lubricant from the lubricating unit 8 is moved towards ground M to be reformed. As the top of the injection rod 1 reaches a predetermined depth, the lubricating unit 8 closes to stop discharging. The component A of the instantaneous hardening type hardening material (or the slow hardening type hardening material) is fed at a super high pressure into the first conduit 2a and the component B of the instantaneous hardening type hardening material (or gas) is fed at a super high pressure into the second conduit 2b. Both the components A and B are injected outwardly from the injection nozzles 3a, 3b, 4a and 4b while the injection rod 1 is moved back while revolving. According to this revolving injection, the components A and B are completely mixed and then an essentially cylindrical hard layer S in the ground M has been generated.

Experiment in sand having N-value 15 to 20 resulted in an excellent reforming effect; that is, the cylindrical hard layer having a large diameter of 3m 70cm was obtained under conditions; injection pressure of 400 kg f/cm$^2$, injection rate of 100 l/min, revolving speed of 8 r.p.m, and back-moving speed of 2cm/min.

As given explanation above, the ground reforming device according to the present invention can inject the instantaneous hardening type hardening material at a super high pressure 200 kg f/cm$^2$ or more. When the instantaneous hardening type hardening material is composed of two components, the two components can be sufficiently and uniformly mixed immediately before application to the ground without back-flowing or leakage. On the other hand, when compressed gas such as air is injected from one injection nozzle and the slow hardening type hardening material is injected from the other nozzle bubbles are generate by mixing the slow hardening type hardening liquid material and compressed gas. The hardening material jet is wrapped with the bubbles and forcibly transported to a wide range by dynamic rupture effect generated when the bubbles are ruptured. Thus greater area will be hardened into a high density cylindrical hard layer by ruptured hardening material. The cylindrical hard layer may be formed in any configuration such as parallel arrangement or alignment as required.

Although the invention has been described in its preferred form with a certain degree of particularity, it is understood that the present disclosure of the preferred form has been changed in the details of construction and the combination and arrangement of parts may be resorted to without departing from the spirit and the scope of the invention as hereinafter claimed. For example, one side of the injection means 3 and 4 or the feeding pipes 6a and 6b may be provided with a regulator valve to control injection condition, or the compressor may be further provided with a regulating means.

What is claimed is:

1. A ground reforming device for instantaneously hardenable multiple component materials, comprising:
   a) an injection rod including first and second coaxial substantially coextensive conduits, said first conduit having an external diameter less than the internal diameter of said second conduit for therewith forming an annular flow space;
   first and second oppositely disposed and radially outwardly directed nozzles secured to said second conduit and communicating with said flow space;
   c) third and fourth nozzles secured to and extending radially outwardly from said first conduit for permitting a first component of an instantaneously hardenable material supplied thereto to flow outwardly therefrom, each of said third and fourth nozzles aligned with and extending into one of said first and second nozzles so that material issuing from said first conduit will intermix with a second component of the instantaneously hardenable material supplied to and issuing from said flow space and the diameter of the opening of said third and fourth nozzles at said first conduit is less than he internal diameter of said first conduit;
   d) means cooperating with each of said conduits for supplying the associated material thereto under pressure;
   e) drive means cooperate with said rod for causing rotary and longitudinal movement thereof;
   f) excavating means are secured to and extending coaxially from said second conduit; and
   g) lubrication means are disposed within said first conduit for selectively discharging lubricant coaxially therefrom as said rod is rotated and longitudinally moved.

2. The device of claim 1, wherein:
   a) lubrication means are disposed within said first conduit for discharging lubricant therefrom as said rod is rotated and longitudinally moved.

3. The device of claim 1, wherein:
   a) means are disposed adjacent said lubrication means for closing said flow space.

4. The device of claim 3, wherein:
   a) said closing means are disposed between said excavating means and said first and second nozzles.

5. The device of claim 1, wherein:
   as) neither of said third and fourth nozzles extends radially outwardly beyond said second conduit.

6. The device of claim 1, wherein:
   a) each of said third and fourth nozzles tapers from said first conduit toward said second conduit.

7. The device of claim 6, wherein:
   a) each of said third ad fourth nozzles has a diameter at said first conduit which exceeds its diameter at said second conduit.

8. The device claim 1, wherein:
   a) each of said conduits is cylindrical.

9. The device of claim 1, wherein:
   a) each of said third and fourth nozzles terminates within the wall of said second conduit.

10. A ground reforming device for applying instantaneously hardenable multiple component materials, comprising:
    a) an injection rod including first and second coaxial substantially extensive conduits, said first conduit having an external diameter less the internal diameter of said second conduit for therewith forming an annular flow space;
    b) first and second oppositely disposed and radially outwardly directed nozzles secured to said second conduit and communicating with said flow spaced;
    c) third and fourth nozzles secured to and extending radially outwardly from id first conduit for permitting a first component of a multiple component instantaneously hardenable material supplied thereto to flow outwardly therefrom, each of said third and fourth nozzles aligned with and extending into one of said first and second nozzles so that the first component of the multiple component instantaneously hardenable material supplied to and issuing from said first conduit will intermix with a cooperating second component of he multiple instantaneously hardenable material supplied to and issuing from said flow space;
    d) mans cooperating with each of said conduits for supplying the associated component of the multiple component instantaneously hardenable material thereto under high pressure;
    e) drive means cooperate with said rod for causing rotary and longitudinal movement thereof; and
    f) lubrication means disposed within said first conduit for selectively discharging lubricant coaxially therefrom as said rod is rotated and longitudinally moved.

11. A ground reforming device for two-component instantaneously hardenable materials, comprising:
    a) an injection rod including first and second coaxial substantially coextensive conduits, said first conduit having an external diameter less than the internal diameter of said second conduit or therewith forming an annular flow space;
    b) firs and second oppositely disposed and radially outwardly directed nozzles secured to said second conduit and communicating with said flow space;
    c) third and fourth nozzles secured to an extending radially outwardly from said first conduit or permitting material therein to flow outwardly therefrom, each of said third and fourth nozzles aligned with and extending into one of said first and second nozzles so that a first component of a two-component instantaneously hardenable material issuing from said first conduit will intermix with a second component of the two-component instantaneously hardenable material issuing from said flow space and thereby to create the instantaneously hardenable material;
    d) means cooperating with each of said conduits for supplying each of he components thereto under pressure;
    e) drive means cooperate with said rod of causing rotary and longitudinal movement thereof;
    f) at least first and second radially spaced excavating means secured to and extending coaxially from said second conduit; and
    g) lubrication means disposed within said first conduit for selectively discharging lubricant therefrom between said excavation means as said rod is rotated and longitudinally moved.

* * * * *